US006554966B1

(12) United States Patent
Kramer et al.

(10) Patent No.: US 6,554,966 B1
(45) Date of Patent: Apr. 29, 2003

(54) PROCESS FOR PREPARING ESSENTIALLY FORMIC ACID-FREE N-ALKYL-N'-METHYLALKYLENEUREAS

(75) Inventors: Andreas Kramer, Freinsheim (DE); Johann-Peter Melder, Böhl-Iggelheim (DE); Heinz Rütter, Hochdorf-Assenheim (DE); Günter Riewe, Dannstadt-Schauernheim (DE); Wolfgang Siegel, Limburgerhof (DE); Hans-Jürgen Weyer, Bobenheim-Roxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 293 days.

(21) Appl. No.: 09/603,195

(22) Filed: Jun. 26, 2000

(30) Foreign Application Priority Data

Jun. 28, 1999 (DE) .......................... 199 29 602

(51) Int. Cl.$^7$ .......................... B01D 3/00; C07D 233/34; C07D 239/02
(52) U.S. Cl. .............................. 203/2; 203/38; 544/315; 548/316.4
(58) Field of Search ................ 203/2, 91, 100, 203/38, 15; 548/316.4, 317; 544/315

(56) References Cited

U.S. PATENT DOCUMENTS

| 4,864,026 A | | 9/1989 | Bickert et al. | |
| 4,970,321 A | | 11/1990 | Betz et al. | |
| 5,292,807 A | * | 3/1994 | Schafer et al. | 525/113 |
| 6,103,898 A | * | 8/2000 | Kramer et al. | 540/460 |

OTHER PUBLICATIONS

Derwent 89–033199/05.

* cited by examiner

Primary Examiner—Virgina Manoharan
(74) Attorney, Agent, or Firm—Keil & Weinkauf

(57) ABSTRACT

The invention relates to a process for preparing essentially formic acid-free N-alkyl-N'-methylalkyleneureas of the formula

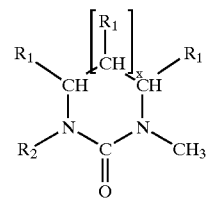

with $R_1$=H or $CH_3$, $R_2=C_nH_{2n+1}$ with n=1–4 and x=0 or 1, from the corresponding alkyleneureas by reaction with monomeric or polymerized formaldehyde in the presence of formic acid. This entails feeding the mixture, obtained in the reaction, of N-alkyl-N'-methylalkyleneurea and formic acid to the upper region of a distillation column, distilling without further additions and removing essentially formic acid-free N-alkyl-N'-methylalkyleneurea in the lower region of the column. The process parameters are set so that the pressure in the upper region of the column is at a higher level than in the lower region of the column, and the difference in pressure between the upper and lower regions of the column is from 10 to 100 mbar, and the temperature in the lower region of the column is higher than in the upper region of the column, with the difference in temperature between the upper and lower regions of the column being from 40° C. to 210° C.

8 Claims, No Drawings

PROCESS FOR PREPARING ESSENTIALLY FORMIC ACID-FREE N-ALKYL-N'-METHYLALKYLENEUREAS

The invention relates to a process for preparing N-alkyl-N'-methylalkyleneureas and, in particular, to the preparation of N,N'-dimethylpropylene- and -ethyleneurea, which are essentially free of formic acid.

N,N'-Dimethylpropyleneurea (DMPU) and the analogous N,N'-dimethylethyleneurea (DMEU) are important as special polar aprotic solvents in agrochemical and drug syntheses. Particularly in reactions with carbanions or carbanion equivalents, DMPU or DMEU can replace the carcinogenic hexamethylphosphoramide. In addition, these N,N'-dimethylalkyleneureas are employed in chemical engineering, for example in extractive distillations to remove cyclohexene from a mixture with benzene and cyclohexane.

The so-called Leuckart-Wallach reaction in particular has become important for preparing such tetrasubstituted ureas and entails reaction of propyleneurea with aldehydes in the presence of formic acid, as described in EP-A 0 301 270.

EP-A 0 280 781 describes the preparation of N-alkyl-N'-methylalkyleneureas and, in particular, of N,N'-dimethylalkyleneureas such as DMPU from propyleneurea and formaldehyde in the presence of formic acid by the so-called Eschweiler-Clark variant.

However, a problem with this is the removal, which should be as complete as possible, by distillation of the formic acid necessary for this reaction. According to EP-A 0 280 781, for complete removal of the formic acid either bases such as alkali metal or alkaline earth metal hydroxides or carbonates are added, or a lower alcohol and a catalytic amount of a mineral acid which serves to esterify the remaining formic acid still present. The ester is then removed by distillation.

Another possibility for essentially complete removal of the formic acid after the reaction is described in EP-A 0 356 973. The formic acid still present in the reaction mixture after the reaction is subjected therein to a thermal decomposition reaction at temperatures of about 120 to 260° C. using a catalyst system composed of a tertiary amine and a copper salt such as CuCl.

It is an object of the present invention, based on this prior art, to develop a process which makes it possible to prepare essentially formic acid-free N-alkyl-N'-methylalkyleneureas and, in particular, to prepare DMPU from propyleneurea and formaldehyde under Eschweiler-Clark conditions without elaborate workup steps.

We have found that this object is achieved by a process for preparing N-alkyl-N'-methylureas which have the formula represented below

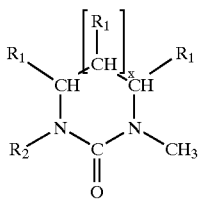

with $R_1$=H or $CH_3$, $R_2=C_nH_{2n-1}$ with n=1–4 and x=0 or 1, from the corresponding alkyleneureas by reaction with monomeric or polymerized formaldehyde in the presence of formic acid, in which an essentially formic acid-free final product is obtained by feeding the mixture, obtained in the reaction, of N-alkyl-N'-methylalkyleneurea and formic acid to the upper region of a distillation column, distilling without further additions and removing essentially formic acid-free N-alkyl-N'-methylalkyleneurea in the lower region of the column, where the pressure in the upper region of the column is set at a higher level than in the lower region of the column, and the difference in pressure between the upper and lower regions of the column is from 10 to 100 mbar, and the temperature in the lower region of the column is set at a higher level than in the upper region of the column, with the difference in temperature between the upper and lower regions of the column being from 40° C. to 210° C. The setting up according to the invention of a predetermined concentration profile in the column makes it possible for the formic acid to be kept in the upper part of the column without the acid breaking through into the N-alkyl-N'-methylalkyleneurea removed as product from the lower part of the column.

It is preferred for the difference in pressure between the upper region of the column, i.e. the top of the column, and the lower region of the column, i.e. the bottom of the column, to be from 20 to 40 mbar and for the difference in temperature to be from 80° C. to 150° C.

The N-alkyl-N'-methylalkyleneurea can be removed in gas form from the lower region of the column. The column which is used preferably has a packing with at least about 30 theoretical plates.

The amount of formic acid still present in the reaction mixture after the reaction is up to 35% by weight. "Essentially formic acid-free" means for the purpose of this invention a formic acid content in the final product of less than 0.1%. The actual reaction of the appropriate alkyleneureas with formaldehyde can be carried out using monomeric or polymerized formaldehyde, such as paraformaldehyde.

In a preferred embodiment of the process according to the invention, the appropriate alkyleneurea is reacted with the formaldehyde and the formic acid at a temperature of from 70 to 150° C. In this connection, the reflux temperature of the reaction mixture under atmospheric pressure, which corresponds to a temperature of about 100 to 110° C., is particularly preferred. It is subsequently possible first to remove the mixture, produced in this reaction, of formic acid and water by distillation. Then, in another step, the considerable amount of formic acid still remaining is removed from the required product.

It has proven particularly suitable to carry out the process in two stages, obtaining the N-alkyl-N'-methylalkyleneurea which is essentially formic acid-free according to the invention in a first step, and carrying out a final distillation to remove near boilers and high boilers in a second step. This increases the space-time yield.

The process is particularly preferably used to prepare N,N'-dimethylpropylene- and -ethyleneurea.

FIRST EXAMPLE a) One-stage Preparation of DMPU

A 4 m³ stirred vessel is charged with 2000 kg of formic acid, 875 kg of propyleneurea and 650 kg of paraformaldehyde and slowly heated to boiling under reflux. After about 8 hours at about 100° C., a mixture of formic acid and water is distilled off under atmospheric pressure up to a vessel temperature of 130° C., and can be returned to the synthesis. The reactor contents, which in each case consist of about 63% DMPU, 30% formic acid, 1.5% water, 2% low boilers and 3.5% high boilers, are cooled and subjected to the distillation. This mixture obtained after the reaction is referred to hereinafter as crude DMPU discharge.

b)

The crude DMPU discharge obtained in the reaction as described under a) is continuously fed into a distillation column with cloth packing which has about 60 theoretical plates, in the upper region of the column, approximately at the 45$^{th}$ plate, and the essentially formic acid-free N,N'-dimethylpropyleneurea is removed in the form of a gas through a side outlet in the lower part of the column in the region of the 10$^{th}$ plate.

The reaction parameters were set so that the pressure at the top of the column was about 200 mbar and the difference in pressure along the column was about 30 mbar.

The temperature in the region of the feed was about 170° C., at the top of column was 107 to 110° C., in the region of the 10$^{th}$ plate was about 190° C. and in the bottom was 200 to 202° C.

The final product removed through the side outlet had the following composition:

>98% DMPU, <0.1% formic acid, <0.1% water.

SECOND EXAMPLE

Two-stage Preparation of DMPU a) Distillation Step 1

The crude DMPU discharge obtained as in Example 1 a) was again fed as described in Example 1 b) into a distillation column and there distilled in a two-stage embodiment. This entailed the low boilers such as formic acid and water being removed in the first distillation step, and near boilers and high boilers being removed from the required final product in the second distillation step. The reaction parameters were set as indicated below:

Distillation Step 1

| | |
|---|---|
| Feed temperature: | 150° C. |
| Temperature at top: | 107–110° C. |
| Temperature at bottom: | 225° C. |
| Vacuum at top: | 200 mbar |
| Difference in pressure: | 20–30 mbar |
| Reflux/feed: | 1:1.75 |
| Composition of bottom discharge: | 94% DMPU, 5% near boilers, <0.1% formic acid, <0.1% water | b) Distillation Step 2

The following distillation parameters were set for the second distillation step:

Distillation Step 2

| | |
|---|---|
| Feed temperature: | 135° C. |
| Temperature at top: | 121–125° C. |
| Temperature at bottom: | 170° C. |
| Vacuum at top: | 200 mbar |
| Difference in pressure: | 20–30 mbar |
| Reflux/feed: | 1:1.5 |
| Composition of the final product at side outlet: | >99.5% DMPU, <0.4% near boilers |

We claim:

1. A process for preparing an N-alkyl-N'-methylalkyleneurea of the formula

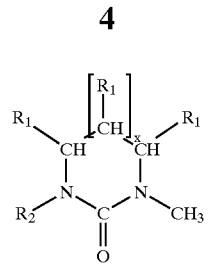

with $R_1$=H or $CH_3$, $R_2=C_nH_{2n+1}$ with n=1–4 and x=0 or 1, wherein the N-alkyl-N'-methylalkyleneurea has a formic acid content of less than 0.1%, by reacting an alkyleneurea with monomeric or polymerized formaldehyde in the presence of formic acid to obtain a reaction mixture comprising the N-alkyl-N'-methylalkyleneurea and formic acid, which process comprises feeding the reaction mixture to the upper region of a distillation column, distilling the reaction mixture in the column, and removing the N-alkyl-N'-methylalkyleneurea in the lower region of the column, wherein the pressure in the upper region of the column is set at a higher level than in the lower region of the column, and the difference in pressure between the upper and lower regions of the column is from 10 to 100 mbar, and the temperature in the lower region of the column is set at a higher level than in the upper region of the column, with the difference in temperature between the upper and lower regions of the column being from 40° C. to 210° C.

2. The process of claim 1, wherein the difference in pressure between the upper and lower regions of the column is from 20 to 40 mbar and the difference in temperature is from 80° C. to 150° C.

3. The process of claim 2, wherein the alkyleneurea is reacted with the formaldehyde and the formic acid at a temperature of from 70 to 150° C., and subsequently a mixture of formic acid and water which is formed in the reaction is firstly distilled of.

4. The process of claim 1, wherein the N-alkyl-N'-methylalkyleneurea is removed as a gas from the lower region of the column.

5. The process of claim 1, wherein the column has a packing with at least about 30 theoretical plates.

6. The process of claim 1, wherein the N-alkyl-N'-methylalkyleneurea is N,N'-dimethylpropyleneurea.

7. The process of claim 1, wherein the N-alkyl-N'-methylalkyleneurea is N,N'-dimethylethyleneurea.

8. A process for preparing an N-alkyl-N'-methylalkyleneurea of the formula

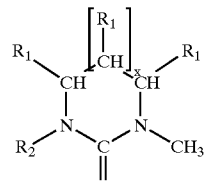

with $R_1$=H or $CH_3$, $R_2=CH_3$ and x=0, wherein the N-alkyl-N'-methylalkyleneurea has a formic acid content of less than 0.1%, by reacting an alkyleneurea with monomeric or polymerized formaldehyde in the presence of formic acid to obtain a reaction mixture comprising the N-alkyl-N'-methylalkyleneurea and formic acid, which process comprises feeding the reaction mixture to the upper region of a distillation column, distilling the reaction mixture in the column, and removing the N-alkyl-N'-methylalkyleneurea as a gas from the lower region of the column, wherein the pressure in the upper region of the column is set at a higher level than in the lower region of the column, and the difference in pressure between the upper and lower regions of the column is from 20 to 40 mbar, and the temperature in the lower region of the column is set at a higher level than in the upper region of the column, with the difference in temperature between the upper and lower regions of the column being from 80° C. to 150° C., whereby a mixture of formic acid and water is firstly distilled off.

* * * * *